(12) United States Patent
Zhang

(10) Patent No.: US 6,720,011 B1
(45) Date of Patent: *Apr. 13, 2004

(54) INJECTABLE COMPOSITION FOR CANCER TREATMENT

(76) Inventor: Ting-Dong Zhang, 5 You Zheng Street, Nan Gang District, Harbin, Harbin 150001 (CN)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/702,011

(22) Filed: Aug. 23, 1996

(30) Foreign Application Priority Data

Aug. 23, 1995 (CN) .......................................... 95108768 A

(51) Int. Cl.$^7$ .......................... A61K 33/36; A61K 9/08
(52) U.S. Cl. ....................................... 424/623; 514/908
(58) Field of Search .......................... 424/623; 514/883, 514/908

(56) References Cited

FOREIGN PATENT DOCUMENTS

WO            95/01789     *    1/1995

OTHER PUBLICATIONS

Huang, S. L. et al., Chinese J: Hematol., vol. 16, 1995, pp. 26–28.*
Kwong, Y. L. et al., "Delicious Poison: Arsenic Trioxide for the Treatment of Leukemia," Blood, vol. 89(9), 1997, pp. 3487–3488.*
Shen, Zhi–Xiang et al., "Use of Arsenic Trioxide ($As_2O_3$) in the Treatment of Acute Promyelocytic Leukemia (Apl) . . . " Blood, vol. 89(9), 1997, p. 3354.*
The Merck Index, 10th ed., Rahway (NJ), Merck & Co., Inc., 1983, p. 117, entry 824.*
Chemical Abstracts 130:115060, 1999.*
Shimotsuura, S. et al., "Studies on the antineoplasmic actions of As2O3," Shikwa Gakuho, vol. 86, pp. 1237–1253, 1986.
Fluka 1995/96 Catalog, p. 152–153, Jul. 1995.*
USP Dictionary of USAN and International Drug Names, United States Pharmacopeial Conventions, Inc., Rockville, MD, p. 59, Nov. 1994.*
Zhang Peng et al., "Treatment of acute promyelocytic Leukemia with intravenous arsenic trioxide," Chinese Journal of Hematology, vol. 17, No. 2, pp. 58–60, Feb. 1996.*
Guo–Qiang Chen et al., "In vitro studies on cellular and molecular mechanisms of arsenic trioxide . . . " Blood, vol. 88, No. 3, pp. 1052–1061, Aug. 1, 1996.*

Shibuya, "Experimental arsenous oxide poisoning," Tokyo Jikeikai Ika Daigaku Zasshi, vol. 86, No. 4, pp. 563–575, 1971.*
Reichl et al., "Effect of arsenic on cellular metabolism after single or repeated injection in guinea pigs," Arch. Toxicol., Suppl. 13, pp. 363–365, 1989.*
Remington's Pharmaceutical Sciences, Mark Publishing Co., Easton, PA, pp. 1570–1580, 1990.*
Zhang Peng et al., "APL Treatment with "713"—Clinical observation on 117 cases and mechanism study," The Academic Journal of Harbin Medical University, Issue 3, p. 243, Jun. 1995.*
Chinese Medical Association, Heilongjiang Branch, "Letter on Historical Facts Regarding the Development of "Ai Ling No. 1" and the Clinical Use of Arsenic Trioxide in the Treatment of Acute Promyelocytic Leukemia and a Study of Its Mechanism," Mar. 27, 1998.*
Zhang, Peng et al., "Clinical Observations and Exploration of Mechanism in the Treatment by 713 of 117 Cases of Acute Promyelocytic Leukemia," The Academic Journal of Harbin Medical University, Issue 3, p. 243, Jun. 14, 1995.*
The Merck Index, 10th ed., Merck & Co., Rahway (NJ), 1983, p. 1098, item # 7479.*
Forkner, C. E. et al., "Arsenic as a therapeutic agent in chronic myelogenous leukemia," The Journal of the American Medical Association, vol. 97, No. 1, Jul. 4, 1931, pp. 3–5.*
Arsenic, Environmental Health Criteria 18, Geneva: WHO, 1981.
Inorganic Arsenic Compounds Other Than Arsine Health and Safety Guide Health and Safety Guide No. 70, WHO, Geneva, 1992.
Sun H.D. et al. The Therapeutical Effect Of Ailing No. 1 (As2O3) on 32 cases with acute promyelocytic leukemia (APL). Chinese Union Journal of Traditional Medicine and Western Medicine, 12:170, 1992.
Ishinishi N. et al. Study on Chronic Toxicity of Arsenic Trioxide in Rats with Special Reference to the Liver Damages. Fukuok Aceta Medicine, 71:27, 1980.

* cited by examiner

*Primary Examiner*—John Pak
(74) *Attorney, Agent, or Firm*—Robert F. Zielinski; Eric A. Dichter

(57) ABSTRACT

An intravenous pharmaceutical composition comprising an aqueous solution of arsenic trioxide and sodium chloride. The composition is effective in the treatment of cancers including leukemia. Complete remission of up to 21 years have been observed for acute promyelocytic leukemia patients.

4 Claims, No Drawings

INJECTABLE COMPOSITION FOR CANCER TREATMENT

The present invention is directed to an injectable, intravenous pharmaceutical composition for the treatment of cancer.

Leukemia is one form of cancer. It is also known as cancer of the blood. It is a life-threatening malignant neoplasm of the hematopoietic system. The survival period of patients diagnosed with the disease is generally about three to six months with no medical intervention. Acute promyelocytic leukemia (APL) is a subtype of leukemia with a high rate of early mortality and a low long-term survival rate where there is lack of medical treatment. Acute myeloid leukemia (AML) is another subtype of leukemia.

In developed countries, the current principal method of cancer treatment is by chemotherapy. For AML, the complete remission rate when treated with chemotherapy is 75% in children and 78% in adults; with a five year disease-free survival (DFS) rate of 35% to 40%. When chemotherapy is combined with bone marrow transplant, the four year DFS is increased to 59%.

In China, the complete remission rate for AML is from 60% to 70%, and the five year DFS is less than 10%.

For APL, it has been shown that with retinoic acid, a complete remission rate of 85% can be achieved. However, it has been found that the relapse rate is high. Where relapse has occurred, it has been found that in re-treatment with the same or similar chemotherapeutic agents, the efficacy is much reduced while the undesirable side effects are enhanced. Most of the patients cannot endure re-treatment and the treatment fails.

The present invention is directed to an intravenous drip composition for the treatment of cancers. The cancers treatable include leukemia, hepatoma and lymphoma.

The effectiveness of the composition of the present invention is demonstrated by clinical trials with patients suffering from APL. The results show that the composition of the present invention is very effective against the cancer cells and produce limited undesirable side effects.

The intravenous composition of the present invention comprises a mixture of arsenic trioxide, sodium chloride and water. More particularly, the composition of the present invention comprises about 1 g–10 g arsenic trioxide, 8 g of sodium chloride and 1000 mL of sterile water suitable for intravenous injection. The composition is prepared by boiling 1000 mL of water, adding the arsenic trioxide to the boiling water and continuing to boil the mixture for a further period of about 30 minutes. After the arsenic trioxide has completely dissolved, the sodium chloride is added. Sterile water is further added to provide a final volume of 1000 mL. The solution is then sterile filtered to ensure injectability by using a G3 glass filter funnel. The filtered solution is introduced into ampules under sterile conditions.

The Pharmacology of the Composition of the Invention

Experimental results demonstrate that the intravenous composition of the present invention exert a strong abruptive effect on the membranes of cancer cells, such as leukemic cells. It inhibits DNA/RNA synthesis and reduces the proliferation of the leukemic cells. The experiments, both in vivo and in vitro have demonstrated that the intravenous composition of the present invention is effective in destroying leukemic cells while inducing increased cell differentiation to produce normal cells. Additionally, the recovery of hematopoietic function is accelerated. It has also been found that the composition of the present invention can pass through the blood-brain barrier.

The increased cell differentiation and formation of normal cells was observed by electronic microscopic tissue examination after treatment with the composition of the present invention.

Method of Administration

An effective daily dose for an adult has been found to be 10 mL of a composition containing 10 g/L of arsenic trioxide added to 500 mL of a 10% glucose solution. The composition can be administered as an intravenous drip. Each course of treatment takes about four weeks. The amount of the composition used should be adjusted based on the concentration of the arsenic trioxide in the composition. The appropriate dose is decreased accordingly for children.

A comparison of the results with other chemotherapeutic agents currently in use shows that higher remission and long term survival rates are obtained with the composition of the present invention. A remission rate of 84% and a DFS of 21 years have been observed.

Laboratory experiments indicate that the composition shows a strong abruptive effect on the membranes of leukemic cells. It also inhibits DNA/RNA synthesis in such cells, reduces the rate of proliferation of leukemic cells and destroys the leukemic cells. The composition also is observed to induce cell differentiation to produce normal cells and restore hematopoietic function. With the composition of the present invention, the development of leukemia in the central nervous system is seldom observed. This indicates that the composition of the present invention can pass through the blood-brain barrier, an obviously superior characteristic over currently used chemotherapeutic agents. Another advantage of the composition of the present invention is that it promotes the proliferation of megakaryotic cells to quickly restore platelet function. As a result, bleeding from hemostatic dysfunction is rare. At the same time, it promotes the production of normal cells by the bone marrow to restore normal hemopoietic function.

A national award for scientific progress second class award has been received for the intravenous composition of the present invention.

The intravenous composition of the present invention comprise 1 g–10 g of arsenic trioxide, 8 g of sodium chloride and sterile water. The composition may be prepared by boiling the ingredients until a clear solution is obtained. The solution is then filtered and sterilized. The detailed procedure for the preparation of the composition comprises boiling 1000 mL of sterile water for injection, adding arsenic trioxide, boiling for a further 30 minutes until the arsenic trioxide is completely dissolved, adding sodium chloride and q.s. with water to 1000 mL. The solution is then sterile filtered through a G3 glass filter funnel and infused into ampules under sterile conditions.

EXAMPLE

Therapeutic Results 110 subjects diagnosed with APL, 69 males and 41 females, with ages ranging from 13 to 65 years, were selected for treatment. The medical history of the patients showed that 91 of the subjects had suffered complications from hemorrhaging to various degrees and 95 of the subjects suffered from various infections. The results of physical examination showed that the Hb (hemoglobin) levels were <100 g/L in 101 patients (91.8%), the WBC (white blood cell) counts were >10×10⁹/L in 82 cases, and the platelet counts were <100×10⁹/L in 106 patients (96.3%). Hypercellularity of bone marrow was observed in 105 patients (95.4%), and the percentage of premyelocyte was >60% in 90 patients (81.8%).

After treatment with the composition of the invention for 2–4 weeks, the WBC counts declined and the bone marrow hemoblasts decreased. Subsequently, both the Hb and platelet counts increased. The myeloblasts and the promyelocytes in the bone marrow were observed to differentiate and the percentage of these blast cells decreased. At the same time, the proliferation of normal blast cells became more pronounced and the number of megakaryocytes increased. The general physical condition of the patients were observed to improve. The results upon completion of treatment indicated that complete remission was achieved in 80% of the patients, partial remission was achieved in 3.6% of the patients. The early mortality rate was 16.4%. The main causes for the early mortality were diagnosed to be due to severe infection and hemorrhage.

Long term follow up with 24 patients who had complete remission for 20 years indicated that: 5 patients died from severe infection and hemorrhaging after 1–4 years of complete remission; 19 patients survived for more than 10 years. Among the 19, 17 patients are still alive. The longest survival period is 21 years at present.

I claim:

1. A method of treating leukemia in humans comprising the steps of:

(a) preparing an aqueous solution consisting of approximately 0.1% to 1.0% by weight arsenic trioxide, 0.8% by weight sodium chloride, 10% by weight gluclose and water;

(b) sterilizing said aqueous solution to form an injectably administrable leukemia treating composition;

(c) administering an effective amount of said composition as an intravenous drip to a human in need of treatment for leukemia; and (d) ceasing the administration of said composition.

2. The method of claim 1, wherein steps (c) and (d) are repeated on a daily basis for approximately 2 to 4 weeks.

3. A method of treating leukemia in humans comprising the steps of:

(a) preparing an aqueous solution consisting of water and 0.1% to 1.0% by weight arsenic trioxide;

(b) sterilizing said aqueous solution to form an injectably administrable leukemia treating composition;

(c) administering an effective amount of said composition as an intravenous drip to a human in need of treatment for leukemia; and (d) ceasing the administration of said composition.

4. The method of claim 3, wherein steps (c) and (d) are repeated on a daily basis for approximately 2 to 4 weeks.

* * * * *